US009207248B2

(12) United States Patent
Nazareth et al.

(10) Patent No.: US 9,207,248 B2
(45) Date of Patent: Dec. 8, 2015

(54) DIAGNOSTIC DETECTION DEVICES AND METHODS

(75) Inventors: Albert R. Nazareth, Mercerville, NJ (US); Timothy Snowden, Howell, NJ (US); Mary-Beth Boyle, Pennington, NJ (US)

(73) Assignee: CHURCH & DWIGHT CO., INC., Princeton, NJ (US)

( * ) Notice: Subject to any disclaimer, the term of this patent is extended or adjusted under 35 U.S.C. 154(b) by 942 days.

(21) Appl. No.: 13/331,509

(22) Filed: Dec. 20, 2011

(65) Prior Publication Data

US 2013/0157379 A1 Jun. 20, 2013

(51) Int. Cl.
*G01N 33/558* (2006.01)
*G01N 33/76* (2006.01)
*G01N 33/543* (2006.01)

(52) U.S. Cl.
CPC .......... *G01N 33/76* (2013.01); *G01N 33/54306* (2013.01); *G01N 33/558* (2013.01)

(58) Field of Classification Search
None
See application file for complete search history.

(56) References Cited

U.S. PATENT DOCUMENTS

| | | | | |
|---|---|---|---|---|
| 4,343,896 | A | * | 8/1982 | Wolters et al. ................... 435/5 |
| 4,624,930 | A | * | 11/1986 | Tanswell et al. .............. 435/7.94 |
| 5,656,503 | A | * | 8/1997 | May et al. ...................... 436/514 |
| 5,739,041 | A | | 4/1998 | Nazareth et al. |
| 6,046,057 | A | | 4/2000 | Nazareth et al. |
| 6,277,650 | B1 | | 8/2001 | Nazareth et al. |
| 6,319,676 | B1 | | 11/2001 | Nazareth et al. |
| 6,767,714 | B2 | | 7/2004 | Nazareth et al. |
| 7,045,342 | B2 | | 5/2006 | Nazareth et al. |
| 7,776,618 | B2 | | 8/2010 | Nazareth et al. |
| 2010/0311188 | A1 | | 12/2010 | Nazareth et al. |
| 2011/0201122 | A1 | | 8/2011 | Nazareth et al. |

\* cited by examiner

*Primary Examiner* — Chris L Chin
(74) *Attorney, Agent, or Firm* — Knobbe Martens (57) ABSTRACT

Described herein are methods and devices for detecting the presence of an analyte in a liquid sample. In some embodiments, methods and devices for the detection of an antigen in a body fluid using a plurality of species-specific antibodies are provided. A sandwich complex may be formed using primary antibodies derived from two different species.

59 Claims, 5 Drawing Sheets

DIAGNOSTIC DETECTION DEVICES AND METHODS

BACKGROUND OF THE INVENTION

1. Field of the Invention

The present invention relates to diagnostic assays for analytes in a liquid sample. In some embodiments, methods and devices for the detection of an analyte in a body fluid using a plurality of species-specific antibodies are provided.

2. Description of the Related Art

Many types of ligand-receptor assays have been used to detect the presence of analytes in body fluids such as saliva, urine or blood. These assays typically involve antigen-antibody reactions, synthetic conjugates comprising enzymatic, fluorescent, or visually observable tags, and specially designed reactor chambers. In most of these assays, there is a receptor (e.g., an antibody) specific for the selected analyte (e.g., antigen), and a means for detecting the presence and/or amount of the antigen-antibody reaction product. Although some commercially available tests are designed to make a quantitative determination, in many circumstances all that is required is a qualitative indication (e.g., positive/negative). Examples of such qualitative assays include blood typing, pregnancy testing, ovulation prediction and many types of urinalysis. For these tests, visually observable indicia, such as the presence of agglutination or a color change, are preferred.

Diagnostic assays should generally be very sensitive because of the often low concentrations of analytes of interest present in a test fluid. False positives can be problematic, particularly with agglutination and other rapid detection methods such as dipstick and color change tests. Because of these problems, sandwich assays which use metal sols or other types of colored particles have been developed that rely on the interaction between avidin and biotin-tagged antibodies. For example, in some commercially available pregnancy tests, an antibody-antigen sandwich complex comprising a colloidal gold-labeled anti-hCG antibody and an anti-hCG biotin-labeled antibody is used.

Because the above disclosed assays and methods enable the formation of antibody-antigen sandwich complexes in the liquid phase of an assay prior to the test line, they allow for more time for antigen recognition and binding to occur. These assays and methods therefore have greater sensitivity and discrimination for analytes of interest, resulting in greater reproducibility, sensitivity, and avoidance of false positives. Although such advances have improved these types of assays, further improvements in reliability and ease of manufacture are desirable.

SUMMARY OF THE INVENTION

The present invention provides rapid, sensitive diagnostic devices and methods for detecting the presence of analytes in body fluids. In preferred embodiments, these methods and devices have high sensitivity and result in virtually no false positives, enabling reliable results even when used by untrained persons.

In preferred embodiments, a mixed-species lateral flow assay is provided, whereby an antibody-antigen sandwich complex is captured at a test result site thorough the recognition of a species-specific antibody in the sandwich complex. The antibodies in this antibody-antigen sandwich complex are derived from different species, allowing an antibody-antigen sandwich complex to be captured at the test line by an antibody that recognizes only one of the species-specific antibodies in the sandwich complex.

A device for determining the presence of an analyte in a liquid sample is provided. The device includes a release medium forming an upstream portion of the device; at least two primary antibodies that recognize the analyte and are derived from at least two different species, where at least two primary antibodies are located in or on the release medium; a capture medium forming a downstream portion of the device; and at least one secondary antibody specific for only one of the at least two primary antibodies, where the at least one secondary antibody is located in or on the capture medium.

In some embodiments, a first one of the at least two primary antibodies is conjugated to a label, and a second one of the at least two primary antibodies is unconjugated. In some embodiments, a first antibody of the at least one secondary antibody is specific for the species from which the second one of the at least two primary antibodies is derived. In some embodiments, a second secondary antibody is located in or on the capture medium that is specific for the species from which the first one of the at least two primary antibodies is derived. In some embodiments, the first and second ones of the at least two primary antibodies in or on the release medium are deposited in or on different locations of the release medium. In some embodiments, the first and second secondary antibodies in or on the capture medium are immobilized in or on different locations of the capture medium. In some embodiments, neither of the two primary antibodies are tagged with a capturable moiety or component such as biotin.

In another embodiment, a device for determining the presence of an analyte in a liquid sample is provided. The device includes a release medium comprising: a labeled conjugate comprising a binding member derived from a first species and a label, where the binding member is reactive with a first epitope of the analyte; and a capturable component derived from a second species, where the capturable component is reactive with a second epitope of the analyte, such that if the analyte is present in the sample, a sandwich complex is formed comprising the labeled conjugate, the analyte, and the capturable component; and a capture medium comprising a capture site for capturing the complex, the capture site having immobilized thereon a capture component having specificity for the capturable component.

In another embodiment, a method of determining the presence of an analyte in a liquid sample is provided. The method includes forming a sandwich complex comprising a first primary antibody derived from a first species, the analyte, and a second primary antibody derived from a second, different species; and capturing the sandwich complex with a secondary antibody specific for only one of the first and second different species.

In another embodiment, a method for determining the presence of an analyte in a liquid sample is provided. The method includes contacting the liquid sample with a release medium comprising: a labeled conjugate comprising a binding member derived from a first species, where the binding member is reactive with a first epitope of the analyte, and where the binding member is labeled with a detectable marker; and a capturable component derived from a second species, wherein the capturable component is reactive with a second epitope of the analyte, such that if the analyte is present in the sample, a complex comprising the labeled conjugate, the analyte and the capturable component is formed. The method further comprises contacting the liquid sample with a capture medium following exposure to the release medium, where the capture medium comprises a capture site for capturing the complex, the capture site having immobilized thereon a capture component having specificity for the capturable component; and determining whether the analyte is present in the liquid sample by detecting the presence of the detectable marker at the capture site.

BRIEF DESCRIPTION OF THE FIGURES

FIGS. 1A and 1B show a perspective view.

FIGS. 2A and 2B show a perspective view.

DETAILED DESCRIPTION OF THE INVENTION

The methods and devices described herein are used to perform immunologically-based diagnostic tests. The devices described herein enable a user to determine with high accuracy and sensitivity the presence or absence of a biological marker which is indicative of a physiological condition or state. For example, the methods and devices described herein can enable untrained personnel to reliably assay a liquid sample for the presence of small quantities of a particular analyte, while avoiding false positives and simplifying test procedures. The devices described herein are ideal for use in over-the-counter test kits, which can enable a consumer to self-diagnose, for example, pregnancy, ovulation, venereal disease and other diseases, infections, or clinical abnormalities which result in the presence of an antigenic substance in a body fluid, including determination of the presence of metabolites of drugs or toxins. Some embodiments involve the use of a biphasic chromatographic substrate to achieve an easily readable, sensitive, reproducible indication of the presence of an analyte, such as human chorionic gonadotropin (hCG), follicle stimulating hormone (FSH), or luteinizing hormone (LH), in a test sample, such as a human urine sample. A variety of analytes can be detected in a variety of liquid samples, including urine, blood, saliva, or any other liquid.

Described herein are detection methods and devices that enable the formation of antibody-antigen sandwiches with antibodies derived from more than one species. Unlike commercially available tests, these devices and methods can be used without chemical modifications (e.g., conjugation or biotinylation) that can alter the activity of antibodies. In addition, these devices and methods can eliminate the need for additional steps during the manufacturing process of detection devices, making the devices simpler, less expensive to manufacture and cost-effective to the end-user.

Figure 1A:
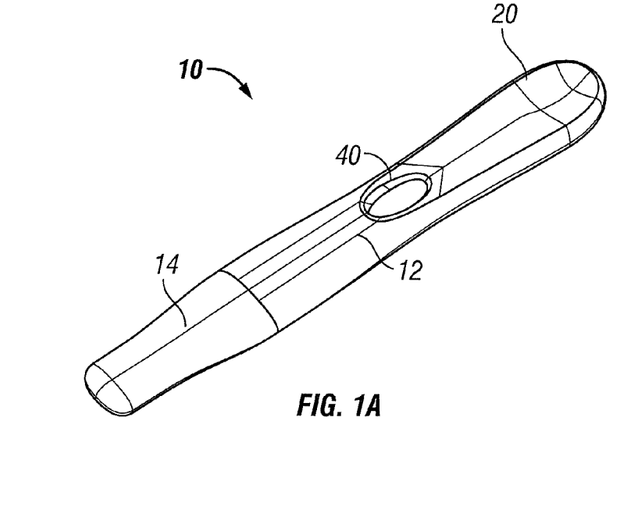
Figure 1B:
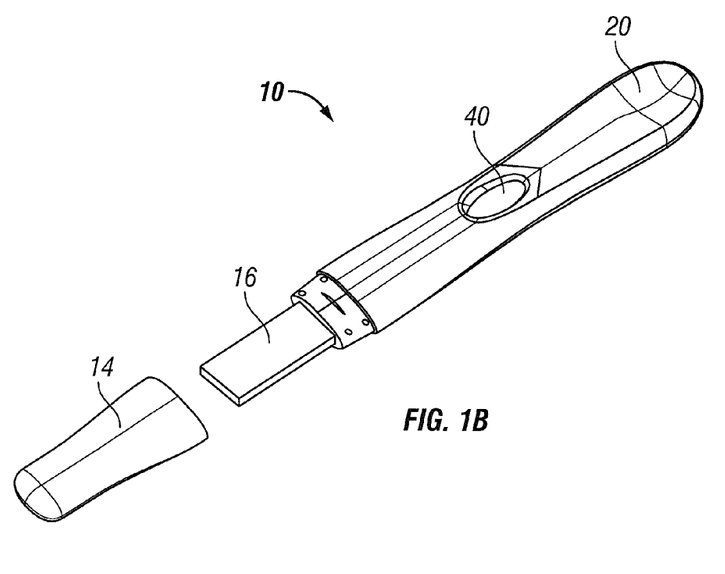
Figure 1C:
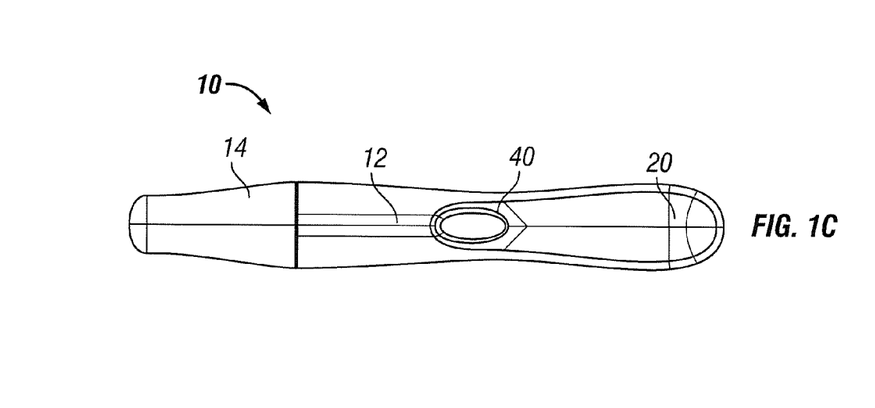
FIG. 1C shows a top view, of an analog detection device.

FIGS. 1A-C illustrate an embodiment of exemplary device 10. FIG. 1A illustrates a perspective view of the device with the cap intact, while FIG. 1B illustrates a perspective view of the device with the cap removed. FIG. 1C illustrates a top view of the device with the cap intact. The device comprises an outer, molded casing 12 which defines a hollow, elongate enclosure. The casing 12 includes a detection opening 40 comprising a window through which a test site (and control site, if applicable) is visible. Casing 12 is configured to provide a recessed portion 20 shaped to permit users to place their thumb into the recessed portion and their forefinger on the bottom of the casing to securely hold the device 10. A central section on the top of the casing 12 defines the centrally located window 40 which permits a user to observe test results on a portion of a lateral flow test strip inside the casing 12, details of which are described further herein. The surface of the test strip in the area of the window 40 may be covered with a clear polymer layer that prevents contamination during use. The device 10 further includes a sample receiving member 16, functioning as a test liquid inlet onto which a liquid sample can be applied to the test strip. Sample receiving member 16 can be covered by a removable cap 14. Sample receiving member 16 is positioned so that part of the sample receiving member is received in the casing enclosure and part of the sample receiving member extends from the end of the casing enclosure. In this embodiment, a test liquid inlet 16 is external to the casing 12 and may be covered by the cap 14 except when in use. Providing the test liquid inlet 16 external to the casing 12 allows for ease of application of the test liquid to the device 10, such as by placing the test liquid inlet 16 in the path of a urine stream or in a container holding the test liquid. The cap 14 is re-attachable (such as by "snap-fitting" onto a lip extending from casing 12) and can be replaced after application of the test liquid to avoid contamination of the sample while the test is proceeding. In this embodiment, the capture sites and control sites visible to the user through the window 40 provide a color or reflectivity change which can be viewed by a user to detect the presence of an analyte and proper functioning of the device.

Figure 2A:
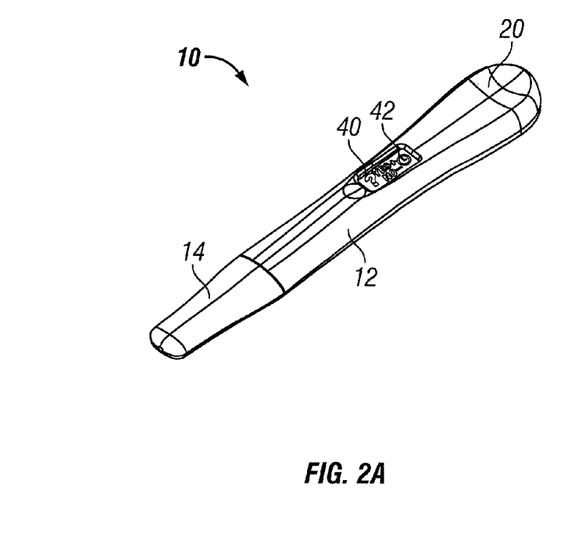
Figure 2B:
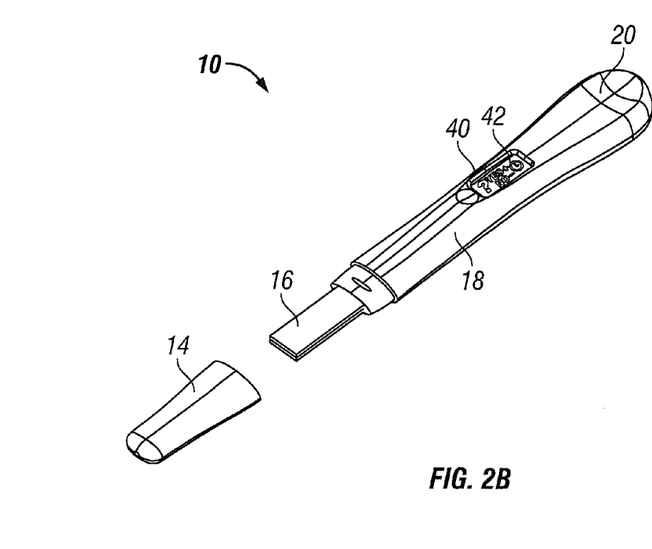
Figure 2C:
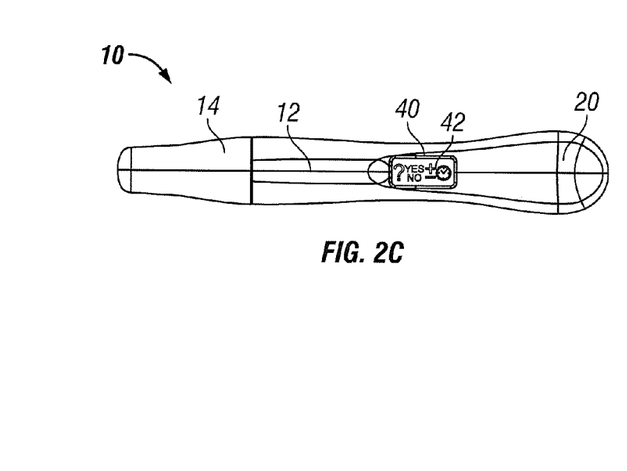
FIG. 2C shows a top view, of a digital detection device.

FIGS. 2A-C illustrate another embodiment of an exemplary device 10. FIG. 2A illustrates a perspective view of the device with the cap intact, while FIG. 2B illustrates a perspective view of the device with the cap removed. FIG. 2C illustrates a top view of the device with the cap intact. The device also comprises an outer, molded casing 12 which defines a hollow, elongate enclosure, and shares many similarities with the device illustrated in FIGS. 1A-1C. Casing 12 is configured to provide a recessed portion 20 shaped to permit users to place their thumb into the recessed portion and their forefinger on the bottom of the casing to securely hold the device 10. A central section on the top of the casing 12 defines a centrally located window 40 which permits a user to observe test results. Inside the casing 12 is a lateral flow test strip and electronic components, details of which will be described further below. Casing 12 defines a sample receiving member 16 onto which a liquid sample can be applied to the test strip in the device. A removable cap 14 can be secured to one end of the casing enclosure over the sample receiving member 16. Sample receiving member 16 is positioned so that part of the sample receiving member is received in the casing enclosure and part of the sample receiving member extends from the end of the casing enclosure. In this embodiment, color or reflectivity changes are sensed electronically, and the results are presented to a user on a display 42. The display 42 may render various icons or messages to a user, such as test results, device status, or error messages. The display 42 may be color or monochrome. In one embodiment, the display 42 is a liquid crystal display (LCD).

Figure 3:
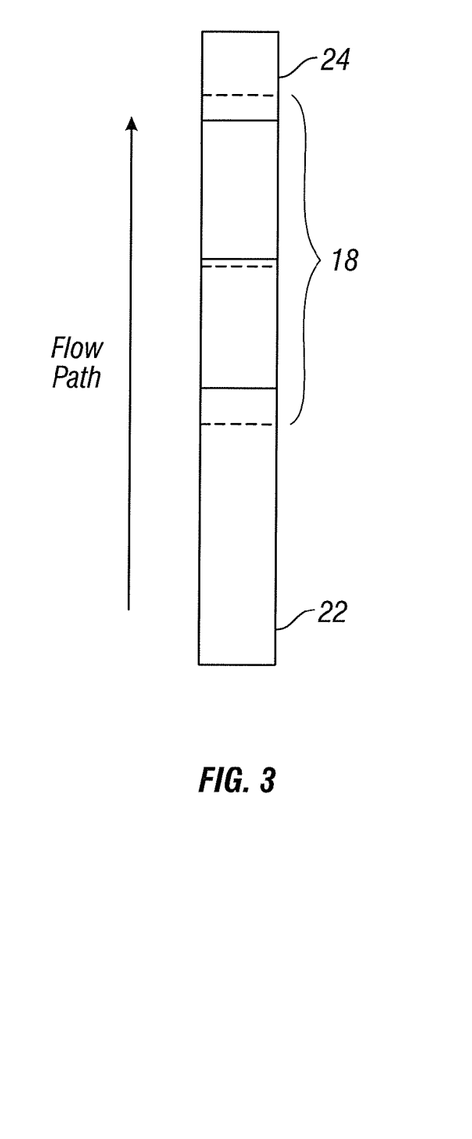
FIG. 3 shows a top view of a lateral flow test strip comprising an absorbent material, a biphasic substrate, and a reservoir material outside of a casing.

FIG. 3 illustrates a preferred embodiment of a test strip. The strip comprises a sample receiving material 22, biphasic chromatographic substrate 18, and reservoir absorbent material 24. When the device is placed in contact with a liquid sample, the liquid is transported by capillary action, wicking, or simple wetting along the flow path downstream through sample receiving material 22, along chromatographic substrate 18, and into reservoir absorbent material 24, generally as depicted by the arrow. Sample receiving material 22 may also serve as a filter which can remove particulate matter and interfering factors from a sample. The sample receiving material 22 preferably is a bibulous hydrophilic material which facilitates absorption and transport of a fluid sample to the biphasic chromatographic substrate 18. Such materials may include cellulose acetate, hydrophilic polyester, or other materials having similar properties. A combination of absorbent materials also may be used. Preferred materials include bonded cellulose acetate, bonded polyolefin or hydrophilic polyester, such as those materials commercially available from American Filtrona Company (Richmond, Va.). Other preferred materials include absorbent papers such as Grade 989 or Grade 939 made of cellulose with polyamide and Grade 1281 made of cellulose and rayon with polyamide, available from Filtertek, Inc. The sample receiving material preferably is coated with a buffered solution containing BSA and a nonionic surfactant, such as Triton X-100. The presence of BSA and surfactant can minimize non-specific absorption of the analyte. For example, a concentration of about 1% BSA and about 0.2% surfactant in tris buffer can be effective for this purpose. As noted above, a filtration means which limits the introduction to the test site of contaminants from the sample may also be included.

Figure 4:
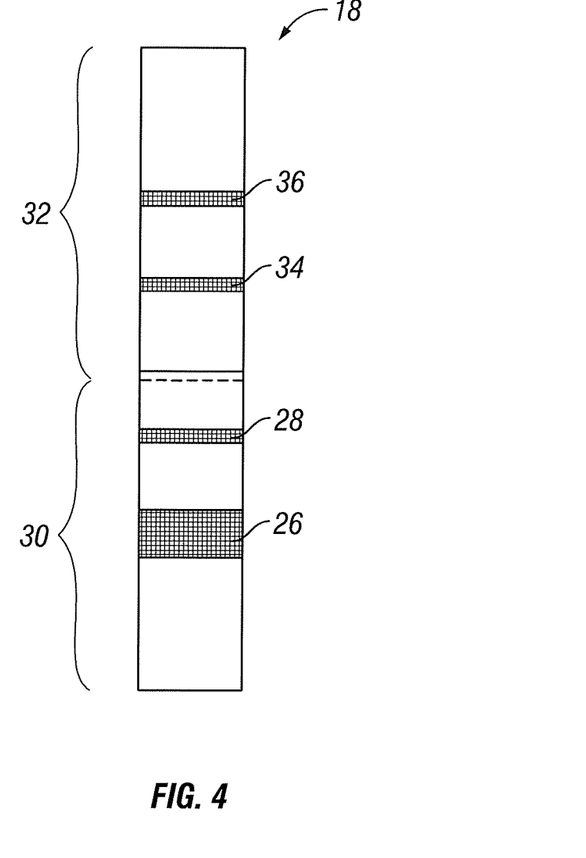
FIG. 4 shows a top view of the biphasic substrate of FIG. 3

FIG. 4 illustrates an exemplary biphasic chromatographic substrate 18, comprising a release medium 30 and a capture medium 32 joined together to form a single liquid path. In some embodiments, the release medium comprises a bibulous, hydrophilic material, such as absorbent paper. Other materials useful in forming the release medium include, for example, cotton linter paper such as S&S 903 and S&S GB002 (available from Schleicher and Schuell, Inc., Keene, N.H.), and BFC 180 (available from Whatman, Fairfield, N.J.); and glass fiber such as Lydall borosilicate (available from Lydall, Inc., Rochester, N.H.). The release medium is also preferably coated with a buffered solution containing BSA and a nonionic surfactant, such as Triton X-100. The presence of BSA and surfactant can minimize non-specific binding and facilitate release of the diffusible reagents. For example, a concentration of about 3% BSA and about 0.1% surfactant can be used.

In some embodiments, the capture medium 32 comprises a hydrophilic polymeric material, preferably a nitrocellulose or nylon membrane. Preferred materials for use as a capture medium are microporous films or membranes which permit protein reagents to be immobilized directly on the membrane by passive adsorption without need for chemical or physical fixation. For this purpose, membranes of nitrocellulose, nylon 6,6 or similar materials are preferred, most preferably having a pore size in the range of from about 5 μm to about 20 μm. Nitrocellulose membranes may be nitrocellulose alone or a mixed ester of nitrocellulose.

Releasably deposited on release medium 30 is a band 26 of dehydrated labeled conjugate binding member, such as an antibody-metal sol specific to a first epitope of the analyte. Metal sols and other types of colored particles useful as marker substances in immunoassay procedures are known to one of skill in the art, such as those in U.S. Pat. No. 4,313,734, which is incorporated herein by reference, including without limitation for the purpose of describing colored particles. Details and engineering principles involved in the synthesis of colored particle conjugates are also known to one of skill in the art, such as those described in Horisberger (Evaluation of Colloidal Gold as a Cytochromic Marker for Transmission and Scanning Electron Microscopy, Biol. Cellulaire, 36, 253-258 (1979)); Leuvering et al. ("Sol Particle Immunoassay", J. Immunoassay 1 (1): 77-91 (1980)), and Frens ("Controlled Nucleation for the Regulation of the Particle Size in Monodisperse Gold Suspensions", Nature, Physical Science, 241: 20-22 (1973)), which are incorporated herein by reference in their entireties.

As the liquid sample moves past band 26, the labeled binding member becomes entrained in the liquid, reconstituted, and reacts or competes with an analyte present in the liquid sample. Disposed downstream of the labeled binding member is a band 28 of dehydrated capturable component. The capturable component comprises a binding member such as an antibody which binds to a second epitope of the analyte. The capturable component also becomes entrained in the liquid sample as it advances along substrate 18. The labeled conjugate and capturable component may be disposed in preserved form, e.g., air dried or freeze-dried, on the release medium 30. Analytes passing through the device contact the labeled conjugate and capturable component, forming a sandwich complex or initiating competition in situ, with the complex ultimately being captured by reagents immobilized on the capture medium as described below.

Immobilized on capture medium 32 are, respectively, capture site 34 and optional control site 36. In FIG. 4, the control and capture sites are illustrated as being disposed serially along the flow path. Alternatively, the control and capture site or sites may be disposed side by side or in other spatial relationships. Capture site 34 comprises a capture component specific for the capturable component deposited on the release medium. Control site 36 comprises immobilized antisera or an antibody specific for the labeled conjugate. This binding agent can be used to capture labeled binding members which are not captured at the upstream capture site. When used, the presence of the detectable marker at the control site indicates that the assay has operated properly.

Polyclonal antisera and monoclonal antibodies or fractions thereof having specific binding properties and affinity for antigenic substances for use with the devices described herein are known to one of skill in the art, and/or can be produced from stable cell lines using cell fusion and screening techniques known to one of skill in the art. The literature provides protocols for producing and immobilizing proteins, such as Laboratory Techniques in Biochemistry and Molecular Biology (Tijssen, Vol. 15), Practice and Theory of Enzyme immunoassays (chapter 13), The Immobilization of Immunoreactants on Solid Phases (pp. 297-328), and the references cited therein, which are incorporated herein by reference in their entireties.

The device may further comprise a reservoir absorbent material 24 disposed downstream of the biphasic chromatographic substrate 18 and in fluid communication therewith. By providing a reservoir of sorbent material disposed beyond the biphasic chromatographic substrate, a relatively large volume of a test liquid containing analytes can be drawn through the test area to aid sensitivity. The reservoir absorbent material preferably comprises a hydrophilic material which may be the same as the upstream sample receiving material, although any absorbent material may suffice. Another purpose of the reservoir absorbent material is to facilitate capillary action along the biphasic chromatographic substrate and to absorb excess liquid contained within the device. The reservoir absorbent material preferably compromises absorbent paper made from cotton long linter fibers, such as S&S 300, S&S 470 and S&S 900 (available from Schleicher & Schuell, Inc.) or cellulosic materials, such as Grade 3 mM (available from Whatman) and Grade 320 (available from Alhstrom).

Figure 5:
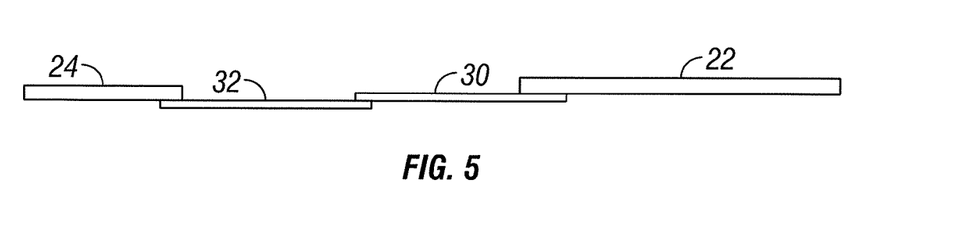
FIG. 5 shows a side view of the test strip of FIG. 3.

FIG. 5 illustrates a side view of a test strip. As shown, sample receiving material 22 is disposed proximate to release medium 30, and overlaps release medium 30 at one end. Release medium 30 in turn overlaps capture medium 32, which is disposed distal to release medium 30. Reservoir absorbent material 24 overlaps the distal end of capture medium 32. These four components together form a single fluid path, and cooperate to cause sample liquid to flow from sample receiving material 22 along release medium 30 and capture medium 32 into reservoir absorbent material 24.

Both the release medium and the capture medium may be laminated onto a polyester film such as MYLAR® or other polymer backing to form a solid phase support. For example, the release and capture media may be laminated onto 5 mil clear PET precoated with an adhesive (available from Adhesives Research).

Upon lamination, the release medium is positioned on top of the capture medium, allowing a small region of overlap between the two media to aid in fluid transfer. This biphasic material containing the assay reagents can be cut into test strips (e.g., as shown in FIG. 4) that can be assembled into a test device (e.g., as shown in FIGS. 1 & 2). Briefly, the release medium and capture medium can be positioned such that they overlap slightly, with an adhesive disposed on the back of each (i.e., the side opposite that which will receive the reagents). The adhesive may be any pressure sensitive or hot melt adhesive which does not fill the pores of the release or capture medium, thereby permitting unimpeded flow of the fluid front through the media. Commercially available adhesives, such as those from Adhesives Research Corp. or Lohmann Precision Die Cutting, LLC, can be used. In a preferred embodiment, the adhesive is disposed on a clear polymer backing. The overlapped release and capture media are then passed through the laminating rollers of a laminating machine together with the backed adhesive, forming a laminate of the capture and release media, the adhesive and the polymer backing. The resulting laminated biphasic substrate is then ready to receive the reagents, which are deposited as continuous stripes onto the top of the substrate. Once the reagents have been deposited and dried, if necessary, the substrate is cut into the desired size.

In some embodiments, the devices and methods described herein utilize a biphasic chromatographic medium which enhances the speed and sensitivity of an assay, such as those described in U.S. Pat. Nos. 6,319,676; 6,767,714; and 7,045,342, which are incorporated herein by reference, including without limitation for the purpose of describing biphasic chromatographic media. Methods for manufacturing biphasic chromatographic media are also described in detail in U.S. Pat. No. 5,846,835, the disclosure of which is hereby incorporated herein by reference in its entirety.

Conventionally, the labeled conjugate at line 26 of FIG. 4 is a gold labeled primary monoclonal antibody having specificity for a first epitope of the analyte. The capturable component at line 28 of FIG. 4 is a second primary monoclonal antibody that is specific for a second epitope of the analyte. These two antibodies are conventionally derived from the same species, such as mouse antibodies. The capturable component antibody is biotinylated. The capture component at line 34 of FIG. 4 is streptavidin. When present, the control line 36 has been formed with monoclonal or polyclonal secondary antibodies specific to the antibodies used at line 26 such as goat anti-mouse antibodies.

The use of the biotin-avidin binding system in these conventional devices has several drawbacks. For example, biotinylation can potentially alter the binding properties of the second primary antibody at line 28. In addition, streptavidin is a hydrophilic protein that is difficult to immobilize onto the capture medium 32. It has the potential of being washed from the medium during the test, blurring and reducing the intensity of the capture line 34 that the user is intended to read. These problems can be resolved with the system described below with reference to FIGS. 6 and 7.

Figure 6:
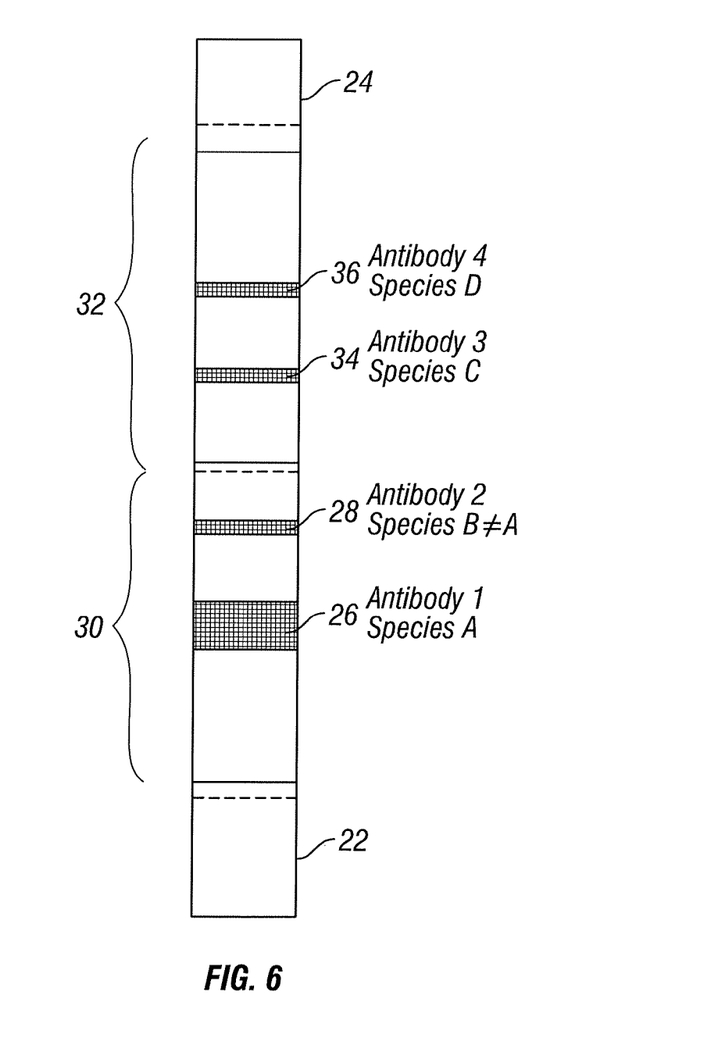
FIG. 6 shows a top view of a test strip comprising an absorbent material, a reservoir, a release medium, a capture medium, and species specific antibodies deposited on the release medium and immobilized on the capture medium.

FIG. 6 illustrates a preferred embodiment of an test strip. As shown, release medium 30 has releasably deposited thereon a band of labeled binding member 26, which in the preferred embodiment is a primary antibody derived from a first species (Species A). Disposed downstream from band 26 is band 28 comprising the capturable component, which in the preferred embodiment is a primary antibody derived from a species other than Species A (referred to here as Species B). Band 28 is also releasably deposited on release medium 30. Located downstream of release medium 30 is capture medium 32 having immobilized thereon capture site 34, which in a preferred embodiment is a secondary antibody derived from a third species (Species C) that is specific for the capturable component. Located on capture medium 32 downstream of capture site 34 is control site 36, which in a preferred embodiment is a secondary antibody derived from a fourth species (Species D) that is specific for the labeled antibody of band 26.

The methods and devices described herein are not limited by the precise nature of the capture site 34 and corresponding control site 36, and in fact, control site 36 may be entirely eliminated if desired. Generally, an antibody or other appropriate affinity agent can be immobilized at capture site 34 and control site 36 using absorption, adsorption, or ionic or covalent coupling, in accordance with methods known to one of skill in the art.

In a preferred embodiment, the methods described herein employ the detection of an antibody-antigen sandwich that is captured at a capture site 34 (or "test line") of a device through the recognition of a species-specific antibody in the sandwich, and an optional control site 36 (or "control line"). This is an improvement over the conventional biotin-avidin system because biotinylation is not needed, and the anti-species antibody is easier to immobilize at the test line 34 than avidin. To accomplish this, the antibodies in an antibody-antigen sandwich are derived from two different species, allowing an antibody-antigen sandwich complex to be captured at the test line by an antibody that recognizes only one of the species-specific antibodies in the sandwich. Potential species-specific origins for the mixed-species embodiments described herein are provided in Table 1.

TABLE 1

Exemplary Combinations for Species-Specific Antibodies

| | Species A | Species B | Species C | Species D |
|---|---|---|---|---|
| Labeled Antibody (Antibody-Antigen Sandwich) | Yes | No | No | No |
| Non-Labeled Antibody (Antibody-Antigen Sandwich) | No | Yes | No | No |
| Test Line Antibody | Yes | No | Yes | Yes |
| Control Line Antibody | No | Yes | Yes | Yes |

For example, if the labeled conjugate antibody is derived from mouse, the non-labeled capturable component antibody can be derived from any species other than mouse. Alternatively, if the non-labeled capturable component antibody is derived from mouse, the labeled conjugate antibody can be derived from any species other than mouse. Further, if the labeled conjugate antibody is derived from mouse, the test line antibody can be derived from mouse (and targeted to the species from which the non-labeled capturable component antibody is derived), and the control site antibody can be derived from any species other than mouse. One of skill in the art will recognize numerous possible combinations of species for the embodiments described herein. Further, one of skill in the art will recognize that antibodies can be derived from any appropriate species, including mouse, sheep, goat, rabbit, llama, etc.

In preferred embodiments, the antibodies described herein have not undergone chemical modification. For example, in some embodiments, antigen-recognizing antibodies are used to capture an antibody-antigen sandwich complex at a test line without employing any components of an avidin-biotin system.

For example, in some embodiments, the presence of a detectable level of hCG in the urine is recognized by a colloidal gold-labeled anti-hCG antibody derived from a first species. After recognition, urine wicking up the release medium results in the formation of an "hCG sandwich complex," whereby the hCG is also detected by the anti-hCG antibody derived from a second species (which recognizes a different epitope or portion of the hCG hormone). This "sandwich complex" is then captured at the test line by a third antibody that is an anti-second species antibody, and the resulting color development at the test line provided by the colloidal gold particles informs the consumer of a positive result (e.g, the presence of hCG in the urine sample).

In one embodiment, a mixed species test strip comprising a gold labeled conjugate antibody derived from Species A, a non-labeled capturable component antibody derived from Species B, a non-labeled antibody derived from Species C (which is anti-Species B), and a non-labeled antibody derived from Species D (which is anti-Species A) is constructed.

When a sample in which an antigen is present is applied to the test strip of this embodiment, fluid moves down the test strip, and the antigen is recognized and bound by a gold-labeled conjugate antibody derived from Species A. As fluid moves further down the test strip, this "half sandwich" is recognized and bound by the non-labeled capturable component antibody derived from Species B. This complete antibody-antigen sandwich then flows to the test line, where it is captured by the immobilized non-labeled antibody that is specific to Species B (e.g., an anti-species B antibody). The gold-labeled antibody derived from Species A allows color to be observed at the test line, informing the user of a positive test result. Excess gold-labeled antibody (which is derived from Species A, and not bound to the anti-species B antibody at test line 34) then flows past the test line and is captured at a control line containing an antibody that is specific to Species A (e.g., an anti-species A antibody).

In contrast, when a sample in which an antigen is not present is applied to the test strip of this embodiment, only the gold-labeled antibody derived from Species A and the unlabeled antibody derived from Species B move up the test strip. Because no antibody-antigen sandwich is formed, only the unlabeled antibody derived from Species B is captured at the test line by the anti-Species B antibody. As a result, no color development occurs at the test line, conveying a negative result to the user. The gold-labeled antibody is then captured at the control line by an anti-Species A antibody.

In one embodiment, a mixed species test strip comprises a gold-labeled conjugate anti-hCG antibody derived from mouse is deposited at line 26, a non-labeled capturable component anti-hCG antibody derived from sheep at line 28, a non-labeled IgG antibody derived from mouse (which is anti-sheep) is immobilized at test line 34, and a non-labeled IgG antibody derived from goat (which is anti-mouse) is immobilized at control line 36.

When a sample containing hCG is applied to the test strip of this embodiment, fluid moves down the test strip, and hCG present in the sample is recognized and bound by the gold-labeled anti-hCG antibody derived from mouse. As fluid moves further down the test strip, this 'half sandwich' is recognized and bound by the non-labeled anti-hCG antibody derived from sheep. This complete antibody-antigen sandwich then flows to the test line, where it is captured by the immobilized mouse-derived anti-sheep IgG antibody at the test line. The mouse-derived gold-labeled antibody in the antibody-antigen sandwich allows color to be observed at the test line, informing the user of a positive test result. Excess anti-hCG gold-labeled antibody (which is derived from mouse, and not bound to anti-sheep IgG antibody at the test line 34) then flows past the test line and is captured at the control line 36 containing a goat-derived anti-mouse IgG antibody.

In contrast, when a sample devoid of hCG is applied to the test strip of this embodiment, only the anti-hCG mouse-derived gold-labeled antibody and the unlabeled anti-hCG sheep-derived antibody move up the test strip. Because no antibody-antigen sandwich is formed, only the unlabeled anti-hCG sheep-derived antibody is captured at the test line by the mouse-derived anti-sheep IgG antibody. As a result, no color development occurs at the test line, conveying a negative result to the user. The gold-labeled antibody is then captured at the control line by a goat-derived anti-mouse IgG antibody.

In some embodiments, the labeled conjugate antibody, capturable component antibody, and test line antibody are derived from three different species. For example, the labeled conjugate antibody could be a mouse derived primary antibody, the capturable component could be a rabbit derived primary antibody, and the test line antibody could be a goat derived anti-rabbit secondary antibody. If the control line is present, it could be derived from a fourth species. If added to the above example, the control line antibody could be a sheep derived anti-mouse secondary antibody.

The methods described herein may be designed to incorporate any conventional "sandwich" or "competitive" techniques known to one of skill in the art. In the case of sandwich techniques, the labeled binding member can comprise an antibody from a first species which binds to an epitope on the analyte of interest to form a labeled antibody-antigen complex. This complex then migrates to react with a capturable component, which comprises a second antibody from a second species that is specific for a second epitope of the analyte, forming a "sandwich" comprising the second antibody, analyte, and labeled antibody. At the capture site, an immobilized capture member binds to the antibody from the second species in the "sandwich." As more and more labeled conjugate is immobilized at the capture site, the colored particles aggregate and become visible through the window of the casing, indicating the presence of the analyte in the liquid sample. Both in the presence or absence of a detectable level of analyte, the colored particles gather at the control site which also is visible through the window.

In the case of competitive techniques, a known amount of the analyte of interest can be labeled and disposed upstream of unlabeled antibodies in the release medium that are specific for the analyte. The labeled analyte may comprise, for example, a sample of the analyte, or a fraction thereof which has comparable specificity for the antibodies. As a liquid sample is transported along the release medium, the labeled analyte and any unlabeled analyte present in the sample compete for sites of attachment to the antibody. If no analyte is present in the sample, labeled analyte-antibody aggregates at the capture site, and the presence of color indicates the absence of detectable levels of analyte in the sample. If analyte is present, the amount of labeled analyte which binds at the test site is reduced because of binding of analyte in the sample with the antibody, and no color, or a paler color, develops. Alternatively, the analyte disposed upstream of the antibodies in the release medium can be labeled with a marker that differs from a marker used for antibodies in the release medium. If analyte is present in the sample, more than one label will be detected at the capture site.

In one embodiment, the methods and devices described herein are designed to detect human pregnancy. In another embodiment, the methods and devices described herein are designed to predict human ovulation. In another embodiment, the methods and devices described herein are designed to determine human fertility status though gauging the ovarian reserve. In another embodiment, the device may be adapted to detect infectious agents, such as streptococcus. Samples for use in conjunction with the methods and devices described herein can include any liquid sample of interest known to one of skill in the art, including without limitation urine, blood, sweat, tears, saliva, or other bodily fluids.

EXAMPLE 1

Construction of Mixed-Species Pregnancy Test Kit

Biphasic test sheets of hydrophilic cellulosic material and nitrocellulose were prepared using production striping procedures and an IVEK linear striper. The release medium portion of the biphasic medium was striped with colloidal gold conjugated with mouse-derived anti-hCG antibody at line 26 of FIG. 6 and sheep-derived anti-hCG antibody at line 28 of FIG. 6. The nitrocellulose portion of the biphasic medium was striped with mouse-derived anti-sheep IgG antibody at test line 34 of FIG. 6 and goat-derived anti-mouse IgG antibody at control line 36 of FIG. 6. The striped biphasic material was allowed to dry overnight at 50° C. The test sheets were then cut into 8 mm test strips and assembled with sample receiving materials and absorbent reservoir materials in device housings.

EXAMPLE 2

Mixed-Species Pregnancy Assay

The devices described in Example 1 were tested in replicates of five in hCG urine standards prepared in negative urine pool (NUP) to contain 0, 25, 50, and 100 mIU hCG/mL. After three minutes, all devices tested in NUP were clearly negative. All devices tested at 25, 50, and 100 mIU hCG/mL gave positive results, and the test lines of those devices were read on a Biodot device to generate quantitative data for color development at the test line (see FIG. 7; each data point is representative of an average of five replicates).

Figure 7:
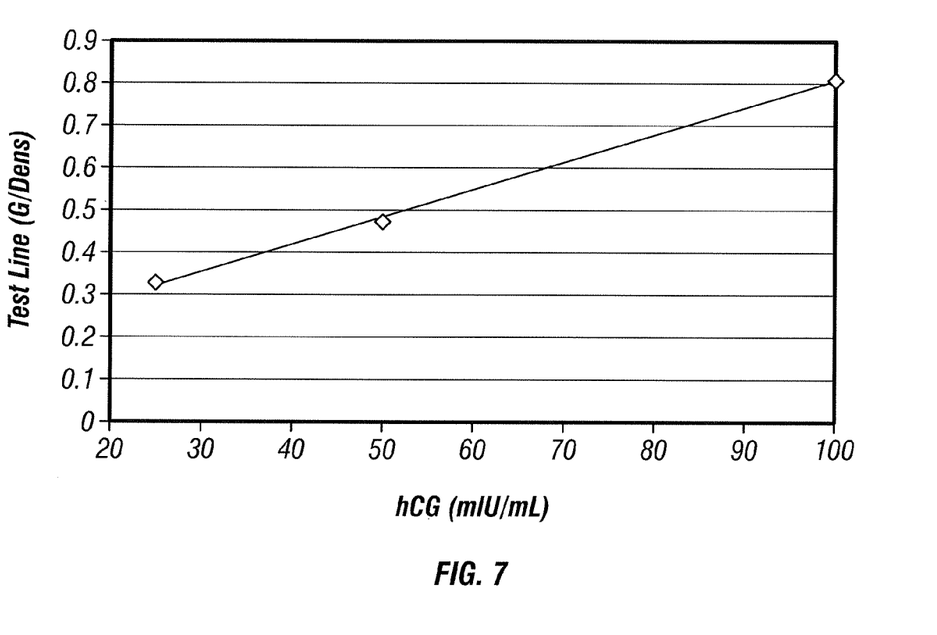
FIG. 7 shows a linear correlation between increasing concentrations of hCG (x-axis) and increasing color intensity (y-axis) for a mixed-species pregnancy assay using the test strip of FIG. 6.

The results in FIG. 7 demonstrate a linear correlation between increasing concentrations of hCG (x-axis) and increasing color intensity of the test line (y-axis). These results indicate that the mouse-derived anti-sheep antibody is effective as a capturing reagent in a mixed-species system, and can specifically capture the mixed-species antibody sandwich complex (e.g., mouse Ab-hCG-sheep Ab) at the test line.

From the foregoing description, one skilled in the art can easily ascertain the essential characteristics of embodiments of this invention, and without departing from the spirit and scope thereof, can make various changes and modifications to adapt it to various usages and conditions. Such embodiments are intended to be included within the scope of the following claims.

What is claimed is:

1. A device for determining the presence of an analyte in a liquid sample, the device comprising:
    a release medium forming an upstream portion of the device;
    at least two primary antibodies that recognize the analyte that are derived from at least two different species, wherein the at least two primary antibodies are located in or on the release medium;
    a capture medium forming a downstream portion of the device;
    at least one secondary antibody specific for only one of the at least two primary antibodies, wherein the at least one secondary antibody is immobilized in or on the capture medium.

2. The device of claim 1, wherein a first one of the at least two primary antibodies is conjugated to a label, and wherein a second one of the at least two primary antibodies is unconjugated.

3. The device of claim 2, wherein a first antibody of the at least one secondary antibody is a species-specific antibody that recognizes only an antibody derived from the species for which it is specific, and wherein the second one of the at least two primary antibodies is derived from that species.

4. The device of claim 3, comprising a second secondary antibody located in or on the capture medium that is a species-specific antibody that recognizes only an antibody derived from the species for which it is specific, and wherein the first one of the at least two primary antibodies is derived from that species.

5. The device of claim 4, wherein the first and second ones of the at least two primary antibodies in or on the release medium are deposited in or on different locations of the release medium.

6. The device of claim 5, wherein the first and second secondary antibodies in or on the capture medium are immobilized in or on different locations of the capture medium.

7. The device of claim 1, wherein neither of the two primary antibodies are biotinylated.

8. A device for determining the presence of an analyte in a liquid sample, the device comprising:
    a release medium comprising:
        a labeled conjugate comprising a binding member derived from a first species and a label, wherein the binding member is reactive with a first epitope of the analyte; and
        a capturable component derived from a second species, wherein the capturable component is reactive with a second epitope of the analyte, such that if the analyte is present in the sample, a sandwich complex is formed comprising the labeled conjugate, the analyte, and the capturable component; and
    a capture medium comprising a capture site for capturing the complex, the capture site having immobilized thereon a capture component having specificity for the capturable component.

9. The device of claim 8, wherein the binding member of the labeled conjugate is an antibody.

10. The device of claim 8, wherein the capturable component is an antibody.

11. The device of claim 8, wherein the capture component is an antibody.

12. The device of claim 8, wherein the capture component is derived from the first species.

13. The device of claim 8, wherein the capture component is an antibody derived from the first species.

14. The device of claim 8, wherein the capture component is derived from a third species.

15. The device of claim 8, wherein the capture component is an antibody derived from a third species.

16. The device of claim 8, wherein the capture medium further comprises a control site having immobilized thereon an agent having specificity for the labeled conjugate.

17. The device of claim 16, wherein the agent having specificity for the labeled conjugate is an antibody.

18. The device of claim 16, wherein the agent having specificity for the labeled conjugate is derived from the second species.

19. The device of claim 16, wherein the agent having specificity for the labeled conjugate is an antibody derived from the second species.

20. The device of claim 16, wherein the agent having specificity for the labeled conjugate is derived from a third species.

21. The device of claim 16, wherein the agent having specificity for the labeled conjugate is an antibody derived from a third species.

22. The device of claim 8, wherein the capture medium further comprises a control site having immobilized thereon an agent having specificity for the labeled conjugate, wherein the capture component is derived from a third species, and wherein the agent is derived from a fourth species.

23. The device of claim 8, wherein the analyte is human chorionic gonadotropin, follicle stimulating hormone, or luteinizing hormone.

24. The device of claim 8, further comprising a sample receiving material located upstream of the substrate at the proximal end of the device.

25. The device of claim 8, further comprising a reservoir absorbent material located downstream of the substrate at the distal end of the device.

26. The device of claim 8, wherein the release medium comprises absorbent material.

27. The device of claim 8, wherein the capture medium is laminated to or cast on a transparent polymeric material.

28. The device of claim 8, wherein the capture medium comprises nitrocellulose or nylon.

29. The device of claim 8, wherein the release medium and the capture medium are both laminated on a single backing support.

30. The device of claim 8, wherein the labeled conjugate comprises a colored particle.

31. The device of claim 30, wherein the colored particle is a gold sol particle.

32. The device of claim 8, further comprising a casing enclosing the release medium and the capture medium, the casing defining a sample inlet in fluid communication with the release medium and one or more detection openings for viewing at least the capture site.

33. The device of claim 32, wherein a control site is visible through the one or more detection openings.

34. The device of claim 32, wherein the detection opening is located on an end of the casing opposite the sample inlet.

35. A method for determining the presence of an analyte in a liquid sample, the method comprising:
    contacting the liquid sample with a release medium comprising:
        a labeled conjugate comprising a binding member derived from a first species, wherein the binding member is reactive with a first epitope of the analyte, and wherein the binding member is labeled with a detectable marker; and
        a capturable component derived from a second species, wherein the capturable component is reactive with a second epitope of the analyte, such that if the analyte is present in the sample, a complex comprising the labeled conjugate, the analyte and the capturable component is formed;
    contacting the liquid sample with a capture medium following exposure to the release medium, wherein the capture medium comprises a capture site for capturing the complex, the capture site having immobilized thereon a capture component having specificity for the capturable component; and
    determining whether the analyte is present in the liquid sample by observing the presence of the detectable marker at the capture.

36. The method of claim 35, further comprising contacting the liquid sample with a control site having immobilized thereon an agent having specificity for the labeled conjugate.

37. The method of claim 35, wherein the binding member of the labeled conjugate is an antibody.

38. The method of claim 35, wherein the capturable component is an antibody.

39. The method of claim 35, wherein the capture component is an antibody.

40. The method of claim 35, wherein the capture component is derived from the first species.

41. The method of claim 35, wherein the capture component is an antibody derived from the first species.

42. The method of claim 35, wherein the capture component is derived from a third species.

43. The method of claim 35, wherein the capture component is an antibody derived from a third species.

44. The method of claim 35, wherein the capture medium further comprises a control site having immobilized thereon an agent having specificity for the labeled conjugate.

45. The method of claim 44, wherein the agent having specificity for the labeled conjugate is an antibody.

46. The method of claim 44, wherein the agent having specificity for the labeled conjugate is derived from the second species.

47. The method of claim 44, wherein the agent having specificity for the labeled conjugate is an antibody derived from the second species.

48. The method of claim 44, wherein the agent having specificity for the labeled conjugate is derived from a third species.

49. The method of claim 44, wherein the agent having specificity for the labeled conjugate is an antibody derived from a third species.

50. The method of claim 35, wherein the capture medium further comprises a control site having immobilized thereon an agent having specificity for the labeled conjugate, wherein the capture component is derived from a third species, and wherein the agent is derived from a fourth species.

51. The method of claim 35, wherein the analyte is human chorionic gonadotropin, follicle stimulating hormone, or luteinizing hormone.

52. The method of claim 35, further comprising applying the liquid sample to a sample receiving material prior to contacting the liquid sample with the release medium.

53. The method of claim 35, wherein at least some of the liquid sample flows to a reservoir absorbent material subsequent to contacting the capture medium.

54. The method of claim 35, wherein the capture medium is laminated to a single backing support.

55. The method of claim 35, wherein the capture medium comprises nitrocellulose or nylon.

56. The method of claim 35, wherein the release medium comprises absorbent material.

57. The method of claim 35, wherein the release medium and the capture medium are both laminated on a single backing support.

58. The method of claim 35, wherein the labeled conjugate comprises a colored particle.

59. The method of claim 58, wherein the colored particle is a gold sol particle.

\* \* \* \* \*